United States Patent
Silverman et al.

(10) Patent No.: US 9,212,161 B2
(45) Date of Patent: Dec. 15, 2015

(54) CHIRAL SYNTHESIS OF PYRROLIDINE CORE COMPOUNDS EN ROUTE TO NEURONAL NITRIC OXIDE SYNTHASE INHIBITORS

(71) Applicant: Northwestern University, Evanston, IL (US)

(72) Inventors: Richard B. Silverman, Winnetka, IL (US); Fengtian Xue, Baton Rogue, LA (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/252,478

(22) Filed: Apr. 14, 2014

(65) Prior Publication Data

US 2014/0228578 A1 Aug. 14, 2014

Related U.S. Application Data

(62) Division of application No. 13/174,982, filed on Jul. 1, 2011, now Pat. No. 8,697,879.

(60) Provisional application No. 61/360,727, filed on Jul. 1, 2010.

(51) Int. Cl.
  *C07D 401/06* (2006.01)
  *C07D 401/12* (2006.01)
  *C07D 493/08* (2006.01)

(52) U.S. Cl.
  CPC ............ *C07D 401/06* (2013.01); *C07D 401/12* (2013.01); *C07D 493/08* (2013.01)

(58) Field of Classification Search
  CPC ... C07D 401/06; C07D 401/12; C07D 493/08
  USPC .............................................. 546/256, 278.4
  See application file for complete search history.

(56) References Cited

U.S. PATENT DOCUMENTS

| | | | |
|---|---|---|---|
| 7,470,790 B2 * | 12/2008 | Silverman et al. | 546/278.4 |
| 7,994,326 B2 * | 8/2011 | Silverman et al. | 546/193 |
| 8,299,100 B2 | 10/2012 | Silverman et al. | |
| 2002/0128490 A1 | 9/2002 | Johnston et al. | |
| 2006/0128789 A1 | 6/2006 | Chand et al. | |
| 2008/0009638 A1 | 1/2008 | Surtees et al. | |
| 2008/0108814 A1 | 5/2008 | Silverman et al. | |
| 2010/0190230 A1 | 7/2010 | Silverman et al. | |
| 2012/0238016 A1 | 9/2012 | Myskens et al. | |

OTHER PUBLICATIONS

Gunnarsson et al. "Preparation and properties . . . " Acta Chemica Scad. 44, 944-951 (1990).*
Hohne et al. "A protection strategy . . . " Adv. Synth. Catal. 350, p. 807-812 (2008).*
Protecting group, Wikipedia, p. 1-9 (2015).*
Silverman et al. "Potent and highly . . . " CA 148:538083 (2008).
Gong et al. "Metabolism of flumatinib . . . " Drug Metabolism and disposition v.38, p. 1328-1340 (2010).
Patani et al. "Bioisosterism: A Rational Approach . . . " Chem. Rev. v.96 p. 3147-3176 (1996).
Xue et al. "Potent and selective neuronal . . . " Bioorg. Med. Chem. Lett v.20, p. 554-557 (2010).
PCT Search Report from PCT/US2011/042758 issued on Feb. 17, 2012.

* cited by examiner

*Primary Examiner* — Celia Chang
(74) *Attorney, Agent, or Firm* — Reinhart Boerner Van Deuren s.c.

(57) ABSTRACT

A chiral synthesis of pyrrolidine compounds en route to selective neuronal nitric oxide synthase inhibitors, and representative inhibitor compounds heretofore unattainable.

7 Claims, No Drawings

CHIRAL SYNTHESIS OF PYRROLIDINE CORE COMPOUNDS EN ROUTE TO NEURONAL NITRIC OXIDE SYNTHASE INHIBITORS

This application is a divisional of and claims priority benefit of application Ser. No. 13/174,982 filed Jul. 1, 2011 and issued as U.S. Pat. No. 8,697,879 on Apr. 15, 2014, which claimed priority benefit of application Ser. No. 61/360,727 filed Jul. 1, 2010, each of which is incorporated herein by reference in its entirety.

This invention was made with government support under Grant No. R01 GM049725 awarded by the National Institutes of Health. The government has certain rights in the invention.

BACKGROUND OF THE INVENTION

Selective inhibition of the activity of neuronal nitric oxide synthase (nNOS) over its closely related isoforms, inducible NOS (iNOS) and endothelial NOS (eNOS), has attracted considerable attention as a target for the treatment of various neurodegenerative diseases such as Parkinson's, Alzheimer's, Huntington's disease, and cerebral palsy. A variety of small molecule scaffolds have been identified that selectively inhibit the activity of nNOS. As part of an effort to find new inhibitors of nNOS, compound 1 was recently prepared and identified as a very potent ($K_i$=5 nM) and highly selective (3800-selective over endothelial NOS, 1200-fold over inducible NOS) nNOS inhibitor. Animal tests demonstrated that 1 could lead to a remarkable reduction in neurological damage to rabbit fetuses under hypoxic conditions. On the basis of these positive results, compound 1 has become a promising lead for further investigation.

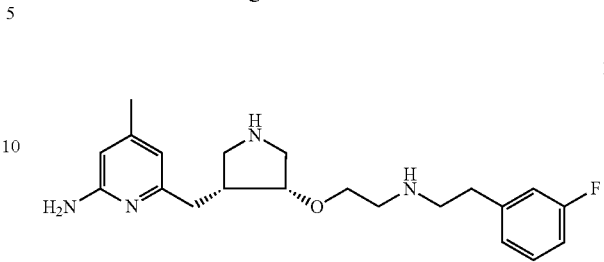

1

Despite this exciting discovery, it is still difficult to achieve gram-scale quantities of 1 for a comprehensive preclinical study because of its challenging synthesis. The previously reported synthetic procedure, shown in Scheme 1, involves 13 steps starting from 4,6-dimethyl-2-aminopyridine. Although this synthesis successfully produced 1, several factors limit scalability. The route was long, and many steps suffered from low yields, resulting in an overall yield of approximately 0.5%. More importantly, the late stage benzyl-deprotection step, involving catalytic hydrogenation of the N-Boc-N-benzyl-protected aminopyridine intermediate 2 (Scheme 1) using a variety of catalytic hydrogenation conditions, proceeded poorly to give 3 with low isolated yields (5-25%).

Scheme 1. Prior art synthetic route to 1.

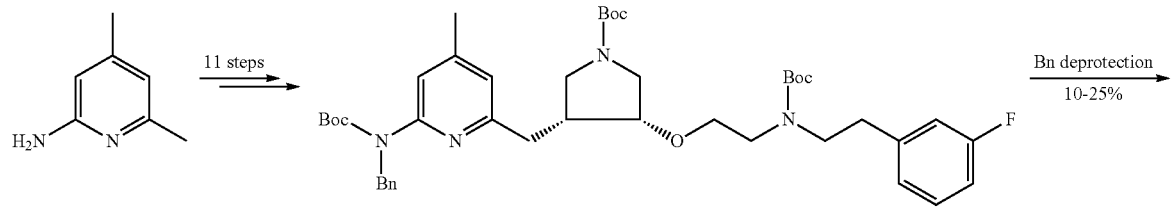

2

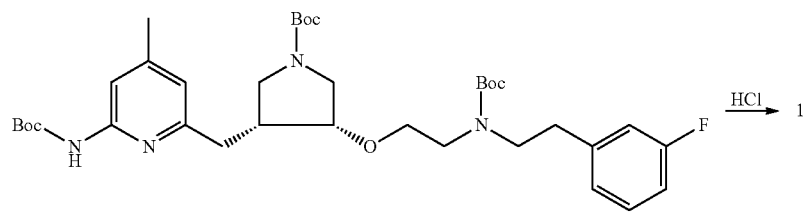

3

Furthermore, the strong reducing conditions used to remove the benzyl-protecting group prohibited the incorporation of reducible functional groups (e.g., nitriles, ketones, alkenes, and halophenyls) into new inhibitors, which significantly limited the structure-activity relationship study of this scaffold. For instance, as summarized in Scheme 2, attempts to synthesize 4 with a similar synthetic route to that of 1 failed because removal of the benzyl-protecting group of 5 using different hydrogenation conditions led to phenyl dehalogenation (6). Removal of the benzyl-protecting group of 7 by catalytic hydrogenation, on the other hand, led to partial reduction of the cyclopropyl ring (8). In addition, the strong reducing conditions led to the reduction of the pyridinyl group in 9 to generate piperidinyl compound 11. Because of the aforementioned difficulties, there remains the need for a more efficient, scalable, and potentially more versatile synthesis of 1 (and related pyrrolidine compounds).

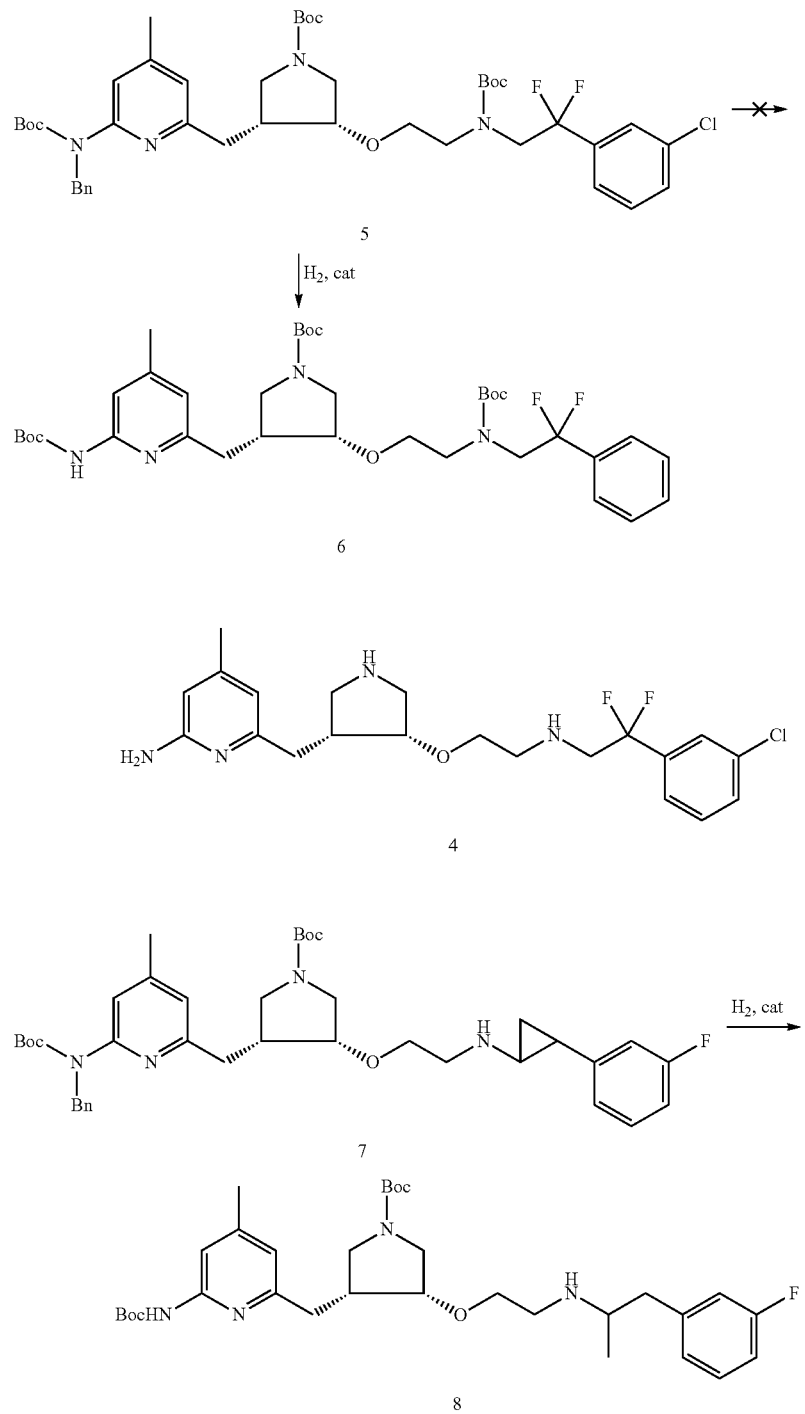

Scheme 2.

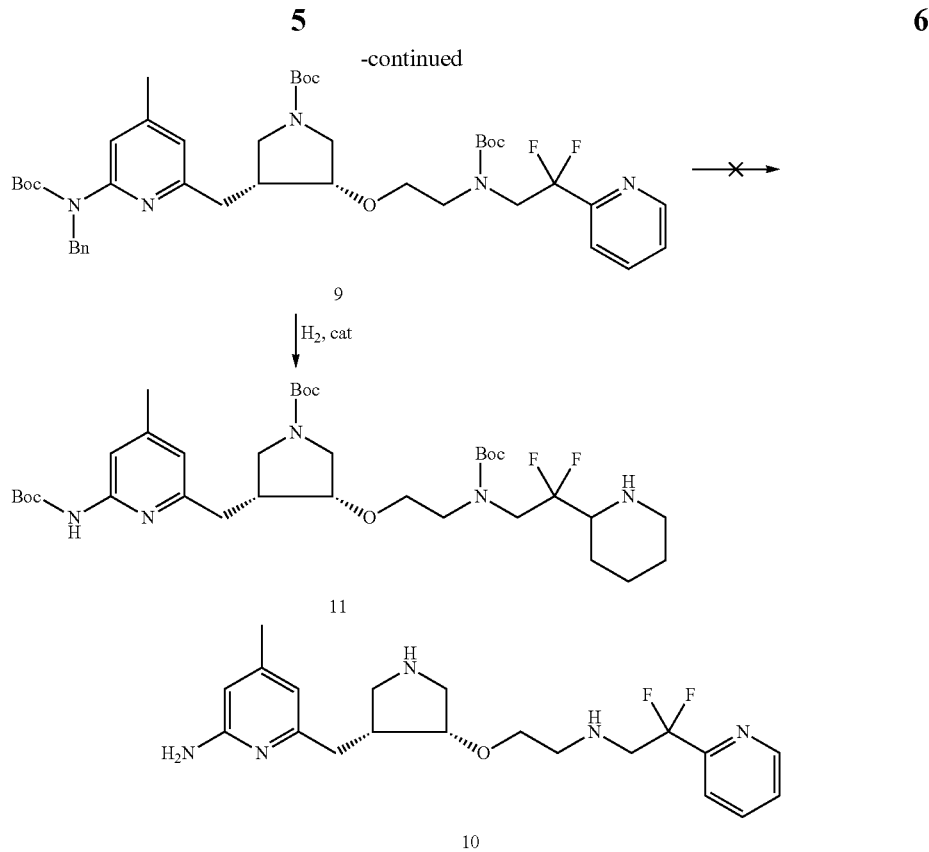

SUMMARY OF THE INVENTION

In light of the foregoing, it is an object of the present invention to provide a chiral synthesis of pyrrolidine core compounds, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally in all its respects, to every aspect of this invention. As such, the following objects can be viewed in the alternative with respect to any one aspect of this invention.

It can be an object of the present invention to provide a cost-effective, efficient route to chiral pyrrolidine compounds of the sort described above and illustrated elsewhere herein.

It can be another object of the present invention, alone or in conjunction with one or more of the preceding objectives, to provide a synthetic approach to a diastereomeric pyrrolidine core compound, en route to a range of NOS inhibitor compounds, including selective nNOS inhibitor compounds.

Other objects, features, benefits and advantages of the present invention will be apparent from this summary and the following descriptions of certain embodiments, and will be readily apparent to those skilled in the art of organic synthesis. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a method of preparing a chiral pyrrolidine core compound. Such a method can comprise providing an N-Boc-protected pyrrolidine-3,4-epoxide; alkylation of such an epoxide with an N-Boc-protected, amino-substituted haloalkylheterocyclic compound to provide a corresponding racemic alkyl-substituted trans-pyrrolidine alcohol; protection of such a pyrrolidine hydroxyl group; Boc-protection of such an amino group on such a heterocyclic substituent; hydroxyl deprotection; resolution of a racemic trans-alcohol by camphanic acid esterification to provide separable diastereomers; and hydrolysis of a chosen enantiomer.

Alternatively, such a method can comprise providing a racemic di-N-Boc-protected 3,4-trans-(aminopyridinyl)alkyl-substituted pyrrolidine alcohol, with such a hydroxyl group as can also be suitably protected; Boc-protection of such an amino group, to provide a tri-Boc-protected heterocyclic compound; removal of any such hydroxyl protecting group; and racemic resolution by camphanic acid esterification with subsequent ester hydrolysis to provide separable diastereomers.

In part, the present invention can also be directed to a method of using sequential amino-protection to prepare a chiral pyrrolidine core compound. Such a method can comprise providing a di-N-Boc-protected 3,4-trans-(aminoheterocyclyl)alkyl-substituted pyrrolidine alcohol; protection of such a pyrrolidine hydroxyl group; Boc-protection of such an aminoheterocyclyl moiety; hydroxyl deprotection; and racemic resolution by camphanic acid esterification with subsequent hydrolysis.

Regardless, such a heterocyclylalkyl-substituted pyrrolidine alcohol can undergo allylation. The allyl moiety can be oxidized to an aldehyde group, then reductively aminated with an ethanamine en route to a corresponding NOS inhibitor compound of the sort described in co-pending application Ser. No. 12/693,196 filed Jan. 25, 2010, the entirety of which is incorporated herein by reference.

Accordingly, the present invention can be directed to a compound of a formula

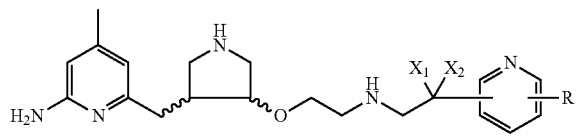

wherein $X_1$ and $X_2$ can be independently selected from H and F; and R can be selected from H, halo and substituted (e.g., without limitation, halo, amino, hydroxy, etc.) alkyl (e.g., without limitation, $C_1$-$C_3$) moieties, and a salt, thereof. In certain embodiments, each of $X_1$ and $X_2$ can be F. In certain other embodiments, R can be H. When present as either a mono-, di- or tri-quaternary ammonium salt, a counter ion can be a conjugate base of a protic acid. Regardless, with respect to the broader aspects of this invention, the present compounds are without stereochemical limitation. Where such compounds and/or their intermediates are available as racemic mixtures, the respective isomers can be resolved. Likewise, as such compounds are diastereomers, the corresponding enantiomers can be separated. Accordingly, any such stereocenter can be (S) or (R) with respect to any other stereocenter(s), whether such a compound is present as a salt, hydrate and/or solvate thereof. For selective inhibition of neuronal nitric oxide synthase, such a compound can be the (R,R) enantiomer.

While the present invention can be illustrated in the context of a 4-methylpyridine moiety conjugated with a pyrrolidine core, will be understood by those skilled in the art that conjugation via alkylation and epoxide ring-opening can be achieved with various other haloalkyl-pyridine and other haloalkylheterocyclic moieties. For example, without limitation, various other heterocyclic moieties including but not limited to substituted and unsubstituted thiazine, oxazine, pyrazine, oxazole and imidazole moieties are described in U.S. Pat. No. 7,470,790 issued Dec. 30, 2008 and co-pending application Ser. No. 11/906,283 filed Oct. 1, 2007, in the context of substructure I as discussed more fully therein, each of which is incorporated herein by reference in its entirety. The corresponding chiral pyrrolidine core compounds can be prepared using synthetic techniques of the sort described herein or straight forward modifications thereof, as would be understood by those skilled in the art and made aware of this invention. Such heterocycle-conjugated compounds, analogous to core compound 12, below, can be used en route to NOS inhibitors, including selective nNOS inhibitors, of the sort described in the aforementioned incorporated references.

DETAILED DESCRIPTION OF CERTAIN EMBODIMENTS

In accordance with certain embodiments of this invention, a new synthetic route is depicted in Schemes 3 and 4. Such an approach not only produces compound 1 in a significantly improved overall yield, but also can be used to generate inhibitor 10 efficiently. As but one departure from the prior art, the problematic benzyl-protecting group previously utilized is replaced by a Boc-protecting group.

As shown in Scheme 3, the synthesis of precursor 12 began with Boc-protected (tert-butyloxycarbonyl) aminopyridine 13. Alkylheterocycle (e.g., a Boc-protected 2-aminopyridine) 13 was treated with two equivalents of n-BuLi, and the resulting dianion was allowed to react with a Boc-protected pyrrolidine epoxide to generate the trans-alcohol (14) in modest yields (see, e.g., Schemes IIIb and I' in conjunction with examples 18-30 and 51-74, respectively, of the aforementioned incorporated '790 patent and/or '283 co-pending application). The hydroxyl group of 14 was protected with tert-butyldimethylsilyl chloride (TBSCl) in the presence of imidazole to give the silyl ether (15) in excellent yields. The free NH group on the pyridine ring was further protected with another Boc-protecting group using $(Boc)_2O$ in the presence of 4-dimethylaminopyridine (DMAP) to yield 16 in high yields, then the silyl ether of 16 was cleaved using tetrabutylammonium fluoride (TBAF) to provide the tri-Boc protected alcohol (17) in very high yields. The two enantiomers of 17 were resolved through camphanic ester derivatives using a Mitsunobu reaction to generate two separable diastereomers (18a and 18b) in excellent yields. Finally, the ester linkage of the desired diastereomer was hydrolyzed using $Na_2CO_3$ to provide chiral precursor 12 in high yields.

Scheme 3. Synthesis of 12.$^a$

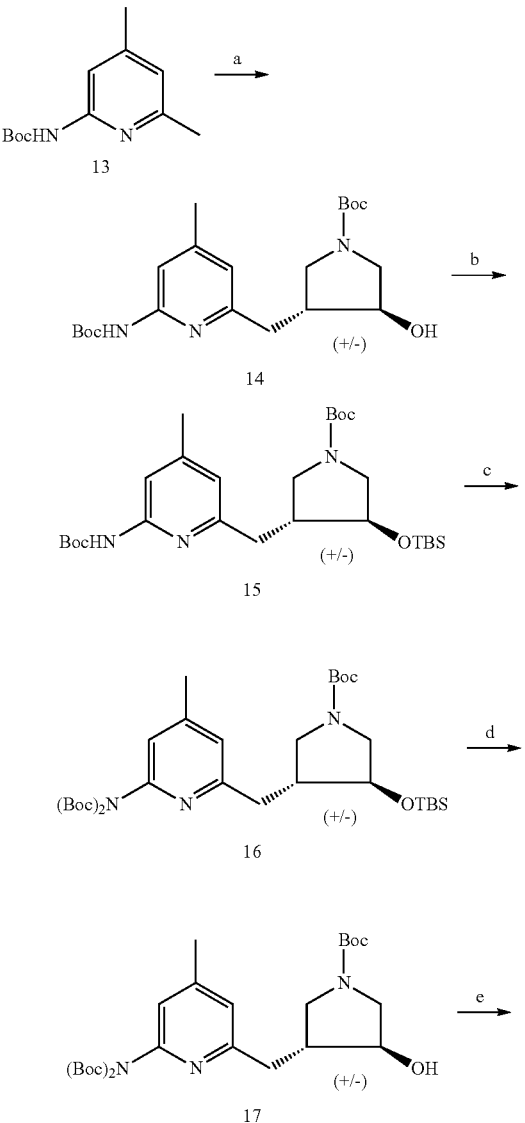

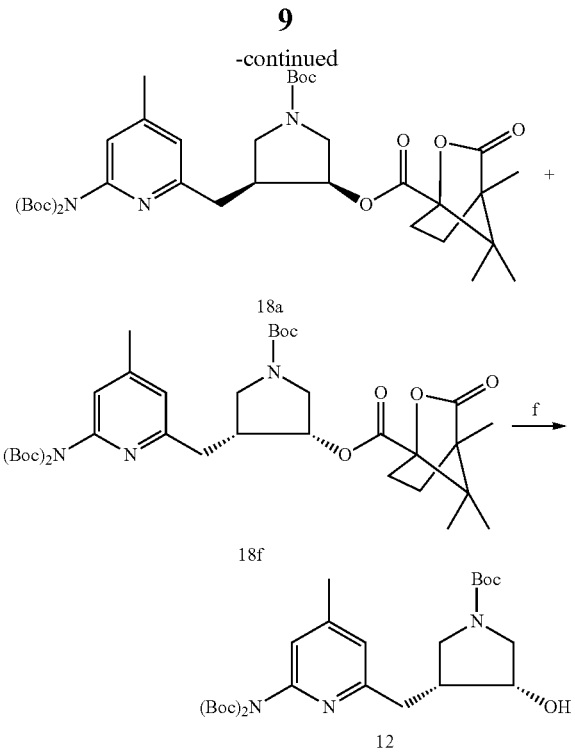

[a] Reagents and conditions: (a) (i) n-BuLi, −78° C. to rt, (ii) epoxide, −78° C. to rt, 41%; (b) TBSCl, imidazole, DMF, rt, 30 h, 93%; (c) (Boc)₂O, DMAP, rt, 24 h, 95%; (d) TBAF, rt, 15 min, 99%; (e) (S)-(−)-camphanic acid, DIAD, rt, 16 h, 94%; (f) Na₂CO₃, H₂O/MeOH, 40° C., 30 min, 97%.

As shown in Scheme 4a, allylation of chiral cis-alcohol 12 (the 3R,4R enantiomer) in the presence of allyl methyl carbonate using Pd(PPh₃)₄ as a catalyst provided 19, quantitatively. Compound 19 was subjected to ozonolysis using Me₂S as reducing reagent to generate aldehyde 20, which underwent reductive amination with, for instance, 2-(3-fluorophenyl)ethanamine or 2,2-difluoro-2-(pyridin-2-yl)ethanamine (Scheme 4a) using NaHB(OAc)₃ to generate secondary amine 21a or 21b, respectively, in good yields. Likewise, as shown in Scheme 4b, reductive amination of the aldehyde with other (halophenyl)ethanamines can be used to generate corresponding secondary amines 22a-d. Finally, the three Boc-protecting groups were removed concurrently in HCl to generate the final inhibitors (1, 4, 10, 23, 24 and 25) in high yields. While the 3R,4R pyrrolidine inhibitors were isolated, as illustrated in Schemes 4a-b, (3S,4S) inhibitor compounds can be prepared from (S,S) chiral precursor 12. (Likewise reductive amination can be achieved with various other substituted phenyl- and substituted pridinylethanamines, such amination limited only by synthetic or commercial availability of the ethanamine starting material. Protecting group removal provides the corresponding pyrrolidine inhibitor compound, analogous to compounds 1, 4, 10 and 23-25).

Scheme 4a. Synthesis of 1 and 10.[a]

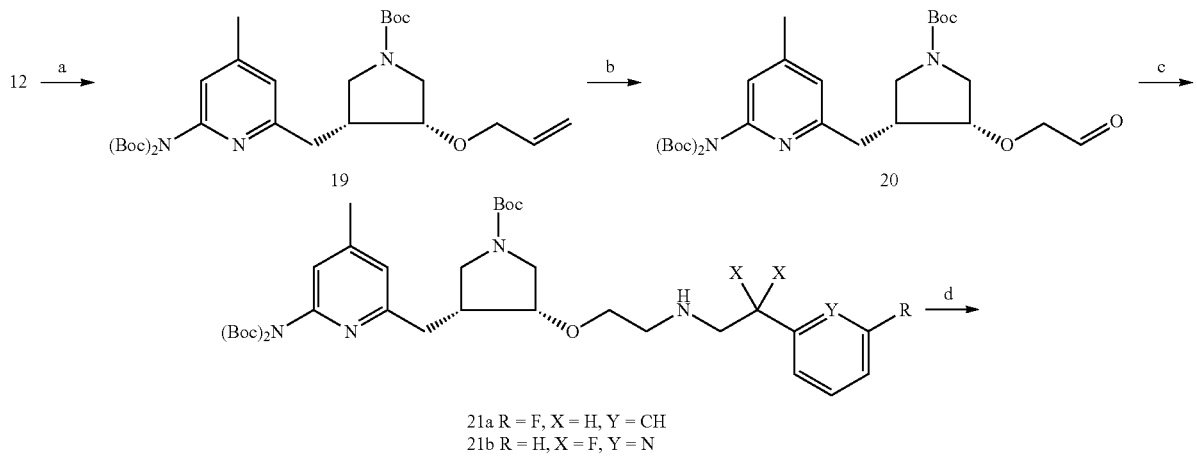

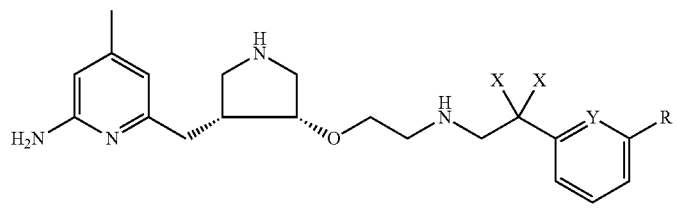

1 R = F, X = H, Y = CH
10 R = H, X = F, Y = N

[a] Reagents and conditions: (a) allyl methyl carbonate, Pd(PPh₃)₄, 45° C., 5 h, 66%;
(b) O₃, -78° C., (ii) Me₂S, -78° C., to rt, 2 h; (c) amine, NaHB(OAc)₃, rt, 3 h, 65-68%;
(d) 6N HCl in MeOH (2:1), rt, 12 h, 97-99%.

Scheme 4b. Synthesis of 4 and 23-25.$^a$

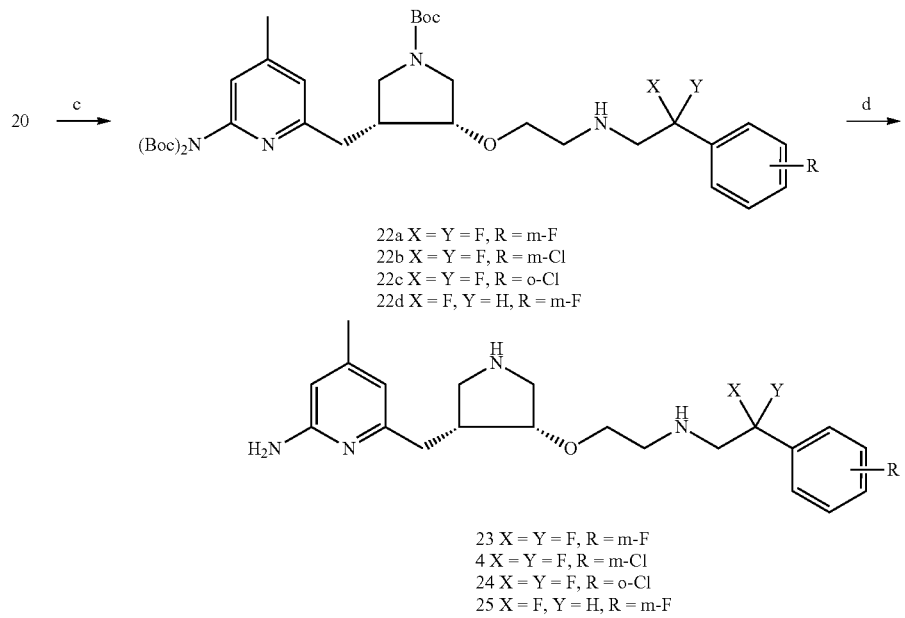

22a X = Y = F, R = m-F
22b X = Y = F, R = m-Cl
22c X = Y = F, R = o-Cl
22d X = F, Y = H, R = m-F

23 X = Y = F, R = m-F
4 X = Y = F, R = m-Cl
24 X = Y = F, R = o-Cl
25 X = F, Y = H, R = m-F $^a$(c) amine hydrochloride, triethylamine, NaHB(OAc)$_3$, rt, 3 h, 86-91%; (d) 6N HCl in MeOH (2:1), rt, 12 h, 90-99%.

EXAMPLES OF THE INVENTION

The following non-limiting examples and data illustrate various aspects and features relating to the methods and/or compounds of the present invention, including the synthesis of various chiral pyrrolidine compounds, as are available through the synthetic methodologies described herein, for use in the preparation of neuronal nitric oxide synthase inhibitors. In comparison with the prior art, the present methods provide results and data which are surprising, unexpected, and contrary thereto. While the utility of this invention is illustrated through the use of several aminoalkylheterocyclic moieties conjugated with a pyrrolidine core, it will be understood by those skilled in the art that comparable results are obtainable with various other heterocyclic moieties conjugated with a corresponding pyrrolidine epoxide, as are commensurate with the scope of this invention.

Example 1

(3R,4S/3S,4R)-tert-butyl 3-((6-(tert-butoxycarbonylamino)-4-methylpyridin-2-yl)methyl)-4-(tert-butyldimethylsilyloxy)pyrrolidine-1-carboxylate (15). To a solution of 14 (2.04 g, 5.0 mmol) in DMF (10 mL) at room temperature was added TBSCl (945 mg, 6.25 mmol) and imidazole (850 mg, 12.5 mmol). (In addition to the aforementioned references, see, also (Lawton, G. R.; Ranaivo, H. R.; Wing, L. K.; Ji, H.; Xue, F.; Martesek, P.; Roman, L. J.; Watterson, D. M.; Silverman, R. B. "Analogues of 2-Aminopyridine-Based Selective Inhibitors of Neuronal Nitric Oxide Synthase with Increased Bioavailability." *Bioorg. Med. Chem.* 2009, 17, 2371-2380), the entirety of which is also incorporated herein by reference.) The reaction mixture was heated at 40° C. for 30 h, and then cooled to room temperature. The solvent was removed by rotary evaporation. The resulting oil was purified by flash column chromatography (EtOAc/hexanes, 1:9, $R_f$=0.25) to yield 15 as a white foamy solid (2.42 g, 93%):

$^1$H NMR (500 MHz, CDCl$_3$) δ −0.01-0.02 (m, 9H), 0.84 (s, 4.5H), 0.85 (s, 4.5H), 1.43 (s, 4.5H), 1.44 (s, 4.5H), 1.50 (s, 9H), 2.27 (s, 1.5H), 2.29 (s, 1.5H), 2.30-2.50 (m, 2H), 2.72-2.77 (dd, J=4.5, 13.0 Hz, 1H), 2.99-3.03 (dd, J=5.5, 11.0 Hz, 0.5H), 3.06-3.16 (m, 1.5H), 3.41-3.44 (dd, J=6.5, 10.5 Hz, 0.5H), 3.51-3.54 (m, 1H), 3.61-3.64 (dd, J=6.0, 11.0 Hz, 0.5H), 3.94-3.97 (m, 1H), 6.59 (s, 1H), 7.11-7.12 (d, J=6.0 Hz, 1H), 7.57-7.59 (d, J=9.5, Hz, 1H); $^{13}$C NMR (125 MHz, CDCl$_3$) δ −4.75, −4.70, 18.0, 21.3, 25.7, 25.8, 28.3, 28.5, 39.0, 39.1, 45.9, 46.4, 48.6, 49.0, 52.5, 52.8, 74.3, 75.1, 80.8, 80.9, 110.15, 110.22, 119.0, 119.1, 149.9, 151.3, 151.4, 152.4, 152.5, 154.7, 157.0, 157.4; LC-TOF (M+H$^+$) calcd for C$_{27}$H$_{48}$N$_3$O$_5$Si 522.3363, found 522.3360.

Example 2

(3R,4S/3S,4R)-tert-butyl 3-((6-(bis(tert-butoxycarbonyl)amino)-4-methylpyridin-2-yl)methyl)-4-(tert-butyldimethylsilyloxy)pyrrolidine-1-carboxylate (16). To a solution of 15 (1.56 g, 3.0 mmol) in THF (30 mL) was added (Boc)$_2$O (980 mg, 4.5 mmol) and DMAP (185 mg, 1.5 mmol). The reaction mixture was allowed to stir at room temperature for 24 h. The solvent was removed by rotary evaporation, and the resulting oil was purified by flash column chromatography (EtOAc/hexanes, 1:9, $R_f$=0.15) to yield 16 as a colorless oil (1.77 g, 95%): $^1$H NMR (500 MHz, CDCl$_3$) δ 0.03-0.05 (m, 6H), 0.87 (s, 4.5H), 0.88 (s, 4.5H), 1.43-1.47 (m, 27H), 2.33 (s, 1.5H), 2.38 (s, 1.5H), 2.50-2.70 (m, 2H), 2.85-2.89 (dd, J=5.0, 13.0 Hz, 0.5H), 2.93-2.98 (dd, J=10.0, 19.0 Hz, 0.5H), 2.99-3.03 (dd, J=6.0, 11.0 Hz, 0.5H), 3.06-3.10 (dd, J=5.0, 10.5 Hz, 0.5H), 3.12-3.17 (m, 1H), 3.42-3.46 (dd, J=6.0, 10.5 Hz, 0.5H), 3.47-3.51 (dd, J=6.5, 11.0 Hz, 0.5H), 3.52-3.56 (dd, J=5.5, 11.0 Hz, 0.5H), 3.63-3.67 (dd, J=6.0, 11.0 Hz, 0.5H), 3.97-4.01 (dd, J=5.5, 11.0 Hz, 0.5H), 4.03-4.06 (dd, J=4.5, 9.5 Hz, 0.5H), 6.85 (s, 1H), 6.93 (s, 0.5H), 6.96 (s, 0.5H); $^{13}$C NMR (125 MHz, CDCl$_3$) δ −4.82, −4.73, −4.66, 17.95, 17.99, 21.0, 25.8, 28.0, 28.5, 38.7, 38.9, 45.9, 46.5, 48.3, 48.7, 52.4, 53.0, 74.3, 75.0, 79.19, 79.24, 82.9, 119.3, 119.5, 122.4, 122.5, 149.5, 149.6, 151.47, 151.53, 151.8, 154.8, 158.5, 158.7; LC-TOF (M+H$^+$) calcd for $C_{32}H_{56}N_3O_7Si$ 622.3888, found 622.3883.

Example 3

(3R,4S/3S,4R)-tert-butyl 3-((6-(bis(tert-butoxycarbonyl)amino)-4-methylpyridin-2-yl)methyl)-4-hydroxypyrrolidine-1-carboxylate (17). To a solution of 16 (3.1 g, 5.0 mmol) in THF (30 mL) was added TBAF (1 M solution in THF, 6.25 mL mg, 6.25 mmol). The reaction mixture was allowed to stir at room temperature for 15 min. The solvent was removed by rotary evaporation, and the resulting oil was purified by flash column chromatography (EtOAc/hexanes, 1:1, $R_f$=0.25) to yield 17 as a white foamy solid (2.48 g, 99%): $^1$H NMR (500 MHz, CDCl$_3$) δ 1.46 (s, 9H), 1.47 (s, 18H), 2.36 (s, 3H), 2.80-2.90 (m, 1.5H), 2.91-2.98 (dd, J=3.5, 14.5 Hz, 0.5H), 3.02-3.08 (dd, J=9.0, 19.0 Hz, 1H), 3.15-3.21 (ddd, J=7.5, 11.0, 18.0 Hz, 1H), 3.62-3.66 (dd, J=8.5, 10.0 Hz, 0.5H), 3.69-3.76 (ddd, J=7.5, 11.5, 18.5 Hz, 1H), 3.78-3.82 (dd, J=7.0, 11.0 Hz, 0.5H), 4.12-4.19 (m, 1H), 4.21 (br s, 0.5H), 4.51 (br s, 0.5H), 6.93 (s, 1H), 6.94-6.95 (d, J=6.0 Hz, 1H); $^{13}$C NMR (125 MHz, CDCl$_3$) δ 14.3, 21.1, 21.2, 28.0, 28.6, 39.4, 39.5, 44.5, 45.5, 49.6, 50.0, 52.4, 52.9, 60.5, 74.5, 75.2, 79.4, 83.5, 120.5, 120.6, 123.3, 123.5, 150.5, 150.7, 151.55, 151.62, 154.5, 154.7, 158.9; LC-TOF (M+H$^+$) calcd for $C_{26}H_{41}N_3O_7$ 508.3023, found 508.3013.

Example 4

Compound 18a and 18b. A mixture of 17 (1.37 g, 2.0 mmol), Ph$_3$P (786 mg, 3.0 mmol), and (1S)-(−)-camphanic acid (475 mg, 2.4 mmol) was dissolved in THF (15 mL) To the resulting solution was added DIAD (590 μL, 3.0 mmol) dropwise at 0° C. The reaction mixture was warmed to room temperature and stirred for an additional 20 h. The solvent was removed by rotary evaporation, and the resulting oil was purified by flash column chromatography (EtOAc/hexanes, 1:4-1:3, $R_f$<0.1) to yield a mixture of 18a (46%): $^1$H NMR (500 MHz, CDCl$_3$) δ 0.93 (s, 3H), 1.02-1.03 (m, 3H), 1.11 (s, 3H), 1.40-1.50 (m, 27H), 1.69-1.73 (ddd, J=4.5, 9.0, 13.5 Hz, 1H), 1.90-1.99 (m, 1H), 2.04-2.12 (ddd, J=4.5, 9.5, 13.5 Hz, 1H), 2.31 (s, 3H), 2.39-2.47 (m, 1H), 2.78-2.90 (m, 1H), 2.91-2.98 (m, 1H), 3.15-3.21 (dd, J=11.0, 14.5 Hz, 1H), 3.45-3.65 (m, 3H), 5.23 (t, J=5.0 Hz, 0.5H), 5.28 (t, J=5.0 Hz, 0.5H), 6.81 (s, 1H), 6.91-6.92 (m, 1H); $^{13}$C NMR (125 MHz, CDCl$_3$) δ 9.5, 14.2, 16.70, 16.72, 16.8, 16.9, 20.9, 21.1, 27.9, 28.4, 28.5, 29.0, 30.8, 30.9, 34.7, 34.8, 41.4, 42.0, 48.9, 49.1, 52.6, 53.1, 54.2, 54.3, 54.8, 60.4, 75.5, 76.2, 79.7, 82.9, 83.0, 90.9, 91.0, 119.9, 120.1, 122.56, 122.59, 149.89, 149.94, 151.38, 151.44, 151.95, 152.00, 154.0, 154.4, 157.7, 166.88, 166.94, 177.9, 178.2; LC-TOF (M+H$^+$) calcd for $C_{36}H_{54}N_3O_{10}$ 688.3809, found 688.3815. and 18b (48%): $^1$H NMR (500 MHz, CDCl$_3$) δ 0.90-1.00 (m, 3H), 1.01-1.10 (m, 3H), 1.14 (s, 3H), 1.40-1.50 (m, 27H), 1.65-1.75 (m, 1H), 1.90-2.00 (m, 1H), 2.01-2.10 (m, 1H), 2.31 (s, 3H), 2.39-2.50 (m, 1H), 2.75-3.02 (m, 3H), 3.10-3.25 (m, 1H), 3.40-3.70 (m, 3H), 5.20 (s, 1H), 6.86 (s, 1H), 6.87-6.95 (m, 1H); $^{13}$C NMR (125 MHz, CDCl$_3$) δ 9.7, 16.6, 16.7, 16.8, 21.0, 22.0, 27.9, 28.41, 28.44, 28.8, 30.4, 34.6, 41.6, 42.2, 48.8, 49.1, 52.6, 53.0, 53.5, 54.3, 54.5, 54.88, 54.94, 70.0, 75.5, 76.2, 79.67, 79.70, 82.9, 83.0, 91.0, 91.2, 119.9, 120.1, 122.8, 149.85, 149.88, 151.35, 151.40, 151.44, 151.9, 154.1, 154.5, 156.4, 157.7, 157.8, 157.9, 167.0, 167.1, 178.3, 178.7; LC-TOF (M+H$^+$) calcd for $C_{36}H_{54}N_3O_{10}$ 688.3809, found 688.3817.

Example 5

(3R,4R)-tert-Butyl 3-((6-(bis(tert-butoxycarbonyl)amino)-4-methylpyridin-2-yl)methyl)-4-hydroxypyrrolidine-1-carboxylate (12). To a solution of 18b (2.1 g, 3.0 mmol) in methanol (60 mL) was added H$_2$O (10 mL) followed by Na$_2$CO$_3$ (636 mg, 6.0 mmol). The reaction was stirred at 40° C. for 30 min and then cooled to room temperature. The reaction mixture was partitioned between DCM (200 mL) and brine (100 mL) The aqueous layer was extracted by DCM (2×100 mL). The combined organic layers were dried over Na$_2$SO$_4$, and concentrated. The crude product was purified by flash column chromatography (EtOAc/hexanes, 1:1, $R_f$=0.2) to yield 12 as a colorless oil (1.48 g, 97%): $^1$H NMR (500 MHz, CDCl$_3$) δ 1.44 (s, 4.5H), 1.45 (s, 4.5H), 1.48 (s, 18H), 2.2-2.36 (m, 1H), 2.37 (s, 3H), 2.77-2.81 (dd, J=5.0, 13.5 Hz, 0.5H), 2.82-2.85 (dd, J=5.0, 13.5 Hz, 0.5H), 2.92-2.97 (t, J=12.5 Hz, 1H), 3.15-3.21 (dt, J=4.5, 10.5 Hz, 1H), 3.37-3.50 (m, 2H), 3.54-3.58 (dd, J=8.0, 10.0 Hz, 0.5H), 3.62-3.66 (dd, J=8.5, 10.0 Hz, 0.5H), 4.04 (br s, 1H), 4.10 (br s, 0.5H), 4.27 (br s, 0.5H), 6.93 (s, 0.5H), 6.95 (s, 0.5H), 6.96 (s, 1H); $^{13}$C NMR (125 MHz, CDCl$_3$) δ 21.0, 28.5, 28.6, 35.0, 35.1, 44.7, 45.4, 49.0, 49.4, 53.3, 53.6, 69.9, 70.7, 79.1, 83.46, 83.51, 120.4, 122.76, 122.84, 150.8, 150.9, 151.4, 151.5, 151.6, 151.7, 154.4, 158.8, 158.9; LC-TOF (M+H$^+$) calcd for $C_{26}H_{41}N_3O_7$ 508.3023, found 508.3013.

Example 6

(3R,4R)-tert-butyl 3-(allyloxy)-4-((6-(bis(tert-butoxycarbonyl)amino)-4-methylpyridin-2-yl)methyl)pyrrolidine-1-carboxylate (19). To a solution of 12 (1.15 g, 2.0 mmol) and Pd(Ph$_3$P)$_4$ (235 mg, 0.2 mmol) in dry THF (50 mL) was added allyl methyl carbonate (700 μL, 6.0 mmol). The reaction mixture was allowed to stir at 45° C. for 5 h and then concentrated. The resulting material was purified by flash column chromatography (silica gel, EtOAc/hexanes, 1:2, $R_f$=0.40) to yield 16 (675 mg, 66%) as a colorless oil: $^1$H NMR (500 MHz, CDCl$_3$) δ 1.40-1.50 (m, 27H), 2.25-2.27 (m, 3H), 2.60-2.75 (m, 1H), 2.78-2.85 (dd, J=9.0, 13.5 Hz, 1H), 2.98-3.05 (dd, J=9.0, 13.5 Hz, 1H), 3.10-3.21 (m, 1H), 3.25-3.29 (dd, J=4.0, 12.5 Hz, 1H), 3.40-3.62 (m, 2H), 3.75-3.85 (m, 2H), 4.00-4.10 (td, J=5.5, 13.0 Hz, 1H), 5.15-5.17 (d, J=10.5 Hz, 1H), 5.25-5.29 (d, J=17.0 Hz, 1H), 5.84-5.91 (ddd, J=5.0, 10.5, 17.0 Hz, 1H), 6.85-6.95 (m, 2H); $^{13}$C NMR (125 MHz, CDCl$_3$) δ 20.9, 27.9, 28.4, 28.5, 34.7, 34.8, 42.7, 43.3, 48.9, 49.2, 50.4, 51.0, 70.2, 70.3, 77.8, 78.6, 79.1, 79.2, 82.8, 116.7, 116.9, 119.6, 122.9, 134.6, 134.7, 149.50, 149.52, 151.4, 151.5, 151.8, 154.5, 154.8, 159.2, 159.3; LC-TOF (M+H$^+$) calcd for $C_{29}H_{46}N_3O_7$ 548.3336, found 548.3339.

Example 7

(3R,4R)-tert-butyl 3-((6-(bis(tert-butoxycarbonyl)amino)-4-methylpyridin-2-yl)methyl)-4-(2-(3-fluorophenethylamino)ethoxy)pyrrolidine-1-carboxylate (21a). A solution of 19 (100 mg, 0.19 mmol) in CH$_2$Cl$_2$ (10 mL) and MeOH (10 mL) was cooled to −78° C., to which O$_3$ was charged until the reaction solution turned purple (~10 min). The O$_3$ flow was stopped, and the reaction was allowed to stir at the same temperature for 10 min. To the resulting solution was added Me$_2$S (150 μL). The reaction mixture was then warmed to room temperature and kept stirring at room temperature for an additional 2 h. The solvent was removed by rotary evaporation to yield aldehyde 20, which was used in the next step without further purification. To a solution of aldehyde 20 in THF (4 mL) was added 2-(3-fluorophenyl)ethanamine (32 mg, 0.23 mmol), followed by NaHB(OAc)$_3$ (50 mg, 0.24 mmol). The reaction mixture was stirred for an additional 3 h and then concentrated. The crude product was purified by flash column chromatography (2.5% MeOH in DCM, R$_f$=0.2) to yield 21a (80 mg, 65%) as a colorless oil: $^1$H NMR (500 MHz, CDCl$_3$) δ 1.40-1.45 (m, 9H), 1.46-1.50 (m, 18H), 2.30-2.31 (m, 3H), 2.55-2.70 (m, 1H), 2.71-2.80 (m, 1H), 2.81-2.90 (m, 1H), 2.95-3.00 (m, 1H), 3.01-3.07 (m, 1H), 3.08-3.20 (m, 4H), 3.21-3.35 (m, 1H), 3.45-3.70 (m, 3H), 3.95-4.15 (m, 2H), 4.95 (br s, 0.5H), 5.19 (br s, 0.5H), 6.65-6.72 (m, 1H), 6.80-6.95 (m, 2H), 6.96-7.03 (m, 1H), 7.15-7.25 (m, 2H); $^{13}$C NMR (125 MHz, CDCl$_3$) δ 21.2, 27.8, 28.0, 28.3, 28.37, 28.45, 28.50, 29.7, 32.8, 33.3, 34.7, 35.0, 42.2, 42.6, 46.0, 46.1, 47.3, 47.5, 48.8, 48.9, 49.06, 49.14, 52.4, 52.7, 53.5, 76.4, 77.9, 79.5, 79.6, 82.2, 82.4, 82.59, 82.62, 113.7, 113.8, 113.9, 115.5, 115.6, 118.6, 120.9, 121.0, 124.4, 130.2, 130.3, 149.8, 150.1, 153.0, 153.2, 153.4, 153.5, 153.6, 153.7, 154.3, 157.1, 157.2, 161.9, 163.9; LC-TOF (M+H$^+$) calcd for C$_{36}$H$_{54}$FN$_4$O$_7$ 673.3977, found 673.3974.

Example 8

(3R,4R)-tert-butyl 3-((6-(bis(tert-butoxycarbonyl)amino)-4-methylpyridin-2-yl)methyl)-4-(2-(3-chlorophenethylamino)ethoxy)pyrrolidine-1-carboxylate (21b). Compound 21b was synthesized using a similar procedure as for 21a (purified by EtOAc/hexanes, 1:2, R$_f$=0.25, 68%): $^1$H NMR (500 MHz, CDCl$_3$) δ 1.43 (s, 9H), 1.49-1.50 (m, 18H), 2.27 (s, 1.5H), 2.28 (s, 1.5H), 2.70-2.85 (m, 2H), 2.88-3.00 (m, 3H), 3.15-3.25 (m, 1H), 3.40-3.61 (m, 5H), 3.90-4.03 (m, 2H), 4.97-5.02 (br s, 0.5H), 5.03-5.09 (br s, 0.5H), 6.52 (s, 1H), 7.20-7.30 (m, 1H), 7.33-7.36 (dd, J=6.0, 6.5 Hz, 1H), 7.64-7.66 (dd, J=2.0, 7.5 Hz, 1H), 7.77-7.80 (dd, J=7.5, 7.5 Hz, 1H), 8.63 (br s, 1H); $^{13}$C NMR (125 MHz, CDCl$_3$) δ 21.12, 21.14, 27.9, 28.0, 28.3, 28.48, 28.51, 29.7, 34.8, 34.9, 41.9, 42.5, 46.7, 46.8, 48.8, 49.0, 49.2, 52.5, 52.9, 53.0, 53.5, 76.6, 79.40, 79.42, 81.2, 82.46, 82.50, 117.8, 120.1, 120.59, 120.62, 124.8, 137.1, 148.7, 149.3, 153.1, 153.2, 154.1, 154.3, 154.4, 157.0; LC-TOF (M+H$^+$) calcd for C$_{35}$H$_{52}$F$_2$N$_5$O$_7$ 692.3835, found 692.3837.

Example 9

6-(((3R,4R)-4-(2-(3-Chlorophenethylamino)ethoxy)pyrrolidin-3-yl)methyl)-4-methylpyridin-2-amine (10). To a solution of 21b (70 mg, 0.10 mmol) in MeOH (2 mL) was added 6 N HCl (4 mL) at room temperature. The mixture was stirred for 12 h and then concentrated. The crude product was purified by recrystallization (EtOH/H$_2$O) to give inhibitor 10 (38 mg, 97%): $^1$H NMR (500 MHz, CDCl$_3$) δ 2.26 (s, 1H), 2.55-2.65 (m, 1H), 2.78-2.85 (dd, J=7.0, 15.0 Hz, 1H), 2.88-2.95 (dd, J=8.0, 15.0 Hz, 1H), 3.02-3.07 (dd, J=15.5, 16.0 Hz, 1H), 3.25-3.33 (m, 2H), 3.39-3.43 (m, 3H), 3.71-3.74 (t, J=6.5 Hz, 2H), 3.89-3.96 (t, J=15.0 Hz, 2H), 4.29 (s, 1H), 6.68 (s, 1H), 6.72 (s, 1H), 7.50-7.53 (dd, J=5.0, 7.5 Hz, 1H), 7.70-7.73 (d, J=8.0 Hz, 1H), 7.92-7.96 (ddd, J=2.0, 8.0, 8.0 Hz, 1H), 8.45-8.55 (d, J=5.0 Hz, 1H); $^{13}$C NMR (125 MHz, CDCl$_3$) δ 21.3, 29.1, 37.8, 42.0, 46.4, 46.9, 50.4, 50.6, 50.8, 53.3, 69.4, 108.0, 114.8, 115.1, 116.7, 118.7, 120.9, 121.0, 126.9, 139.1, 147.4, 149.2, 149.4, 149.6, 149.8, 152.5, 159.3; LC-TOF (M+H$^+$) calcd for C$_{20}$H$_{28}$F$_2$N$_5$O 392.2262, found 392.2265.

Example 10

(3R,4R)-tert-butyl 3-((6-(bis(tert-butoxycarbonyl)amino)-4-methylpyridin-2-yl)methyl)-4-(2-(3-fluorophenethylamino)ethoxy)pyrrolidine-1-carboxylate (22a). To a solution of aldehyde 20 (100 mg, 0.18 mmol) in DCM (4 mL) was added 2,2-difluoro-2-(3-fluorophenyl)ethanamine hydrochloride (83 mg, 0.36 mmol), triethylamine (11 μL, 0.36 mmol), followed by NaHB(OAc)$_3$ (100 mg, 0.45 mmol). The reaction mixture was stirred for an additional 3 h and then concentrated. The crude product was purified by flash column chromatography (EtOAc/hexanes, 1:1, R$_f$=0.15) to yield 22a (115 mg, 91%) as a colorless oil: $^1$H NMR (500 MHz, CDCl$_3$) δ 1.45 (s, 27H), 2.00-2.03 (m, 1H), 2.20-2.25 (m, 3H), 2.60-2.80 (m, 2H), 2.75-2.85 (m, 2H), 2.85-2.95 (m, 1H), 3.00-3.25 (m, 4H), 3.26-3.40 (m, 2H), 3.45-3.50 (m, 1H), 3.50-3.60 (m, 2H), 3.70-3.80 (m, 1H), 3.90-4.00 (t, J=10.5 Hz, 1H), 6.80-6.85 (m, 1H), 6.86-6.90 (m, 1H), 7.00-7.15 (m, 1H), 7.16-7.30 (m, 2H), 7.35-7.45 (m, 1H); $^{13}$C NMR (125 MHz, CDCl$_3$) δ 21.2, 27.8, 28.0, 28.3, 28.37, 28.45, 28.50, 29.7, 32.8, 33.3, 34.7, 35.0, 42.2, 42.6, 46.0, 46.1, 47.3, 47.5, 48.8, 48.9, 49.06, 49.14, 52.4, 52.7, 53.5, 76.4, 77.9, 79.5, 79.6, 82.2, 82.4, 82.59, 82.62, 113.7, 113.8, 113.9, 115.5, 115.6, 118.6, 120.9, 121.0, 124.4, 130.2, 130.3, 149.8, 150.1, 153.0, 153.2, 153.4, 153.5, 153.6, 153.7, 154.3, 157.1, 157.2, 161.9, 163.9; LC-TOF (M+H$^+$) calcd for C$_{36}$H$_{52}$F$_3$N$_4$O$_7$ 709.3788, found 709.3801.

Example 11

(3R,4R)-tert-butyl 3-((6-(bis(tert-butoxycarbonyl)amino)-4-methylpyridin-2-yl)methyl)-4-(2-(3-chlorophenethylamino)ethoxy)pyrrolidine-1-carboxylate (22b). Compound 22b was synthesized using a similar procedure to that of 22a (90%): $^1$H NMR (500 MHz, CDCl$_3$) δ 1.45 (s, 27H), 1.85-1.95 (m, 1H), 2.30-2.35 (m, 3H), 2.55-2.75 (m, 2H), 2.80-2.90 (m, 1H), 2.90-3.00 (m, 1H), 3.05-3.15 (m, 1H), 3.15-3.35 (m, 3H), 3.35-3.50 (m, 2H), 3.50-4.10 (m, 4H), 6.85-6.90 (m, 1H), 6.90-6.95 (m, 1H), 7.30-7.45 (m, 3H), 7.52 (s, 1H); $^{13}$C NMR (125 MHz, CDCl$_3$) δ 27.9, 28.3, 28.4, 28.5, 29.7, 30.6, 34.5, 34.6, 36.6, 42.6, 42.7, 43.2, 48.8, 49.1, 49.2, 49.3, 50.3, 50.8, 53.4, 60.4, 64.4, 68.4, 68.6, 78.6, 79.2, 79.3, 82.8, 92.2, 119.6, 122.8, 123.6, 123.7, 125.7, 125.8, 129.8, 129.9, 130.1, 134.5, 149.7, 151.5, 151.8, 154.5, 154.8, 159.0, 159.1; LC-TOF (M+H$^+$) calcd for C$_{36}$H$_{52}$ClF$_2$N$_4$O$_7$ 725.3493, found 725.3493.

Example 12

(3R,4R)-tert-butyl 3-((6-(bis(tert-butoxycarbonyl)amino)-4-methylpyridin-2-yl)methyl)-4-(2-(2-chlorophenethylamino)ethoxy)pyrrolidine-1-carboxylate (22c). Compound 22c was synthesized using a similar procedure to that of 22a (88%): $^1$H NMR (500 MHz, CDCl$_3$) δ 1.47 (s, 27H), 1.60-1.85 (m, 1H), 2.30-2.33 (m, 3H), 2.55-2.75 (m, 2H), 2.80-2.85 (m, 2H), 2.90-3.95 (m, 1H), 3.05-3.15 (m, 1H), 3.25-3.35 (m, 2H), 3.35-3.50 (m, 4H), 3.50-3.60 (m, 1H), 3.70-3.80 (m, 1H), 6.85-6.87 (d, J=9.5 Hz, 1H), 6.90-6.92 (d, J=11.0 Hz, 1H), 7.30-7.40 (m, 2H), 7.40-7.45 (d, J=12.5 Hz, 1H), 7.60-7.64 (dd, J=1.5, 12.0 Hz, 1H); $^{13}$C NMR (125 MHz, CDCl$_3$) δ 14.1, 27.9, 28.5, 29.7, 34.6, 34.7, 36.6, 42.6, 43.2, 48.7, 49.1, 49.2, 49.3, 50.3, 50.8, 53.5, 68.5, 68.7, 78.6, 79.2, 79.3, 79.4, 82.9, 119.5, 119.6, 122.8, 126.8, 128.2, 128.3, 131.2, 131.4, 149.6, 151.4, 151.5, 151.8, 154.5, 154.8, 159.0, 159.1; LC-TOF (M+H$^+$) calcd for C$_{36}$H$_{52}$ClF$_2$N$_4$O$_7$ 725.3493, found 725.3479.

Example 13

(3R,4R)-tert-butyl 3-((6-(bis(tert-butoxycarbonyl)amino)-4-methylpyridin-2-yl)methyl)-4-(2-(2-chlorophenethylamino)ethoxy)pyrrolidine-1-carboxylate (22d). Compound 22d was synthesized using a similar procedure to that of 22a (86%): $^1$H NMR (500 MHz, CDCl$_3$) δ 1.47 (s, 27H), 2.30-2.35 (m, 3H), 2.60-2.80 (m, 2H), 2.80-2.88 (m, 2H), 2.88-3.00 (m, 2H), 3.05-3.15 (m, 2H), 3.27-3.33 (m, 1H), 3.33-3.45 (m, 2H), 3.45-3.70 (m, 2H), 3.74-3.80 (m, 1H), 5.50-5.80 (m, 1H), 6.85-6.90 (m, 1H), 6.90-6.92 (m, 1H), 7.00-7.05 (m, 1H), 7.05-7.20 (m, 2H), 7.30-7.35 (m, 1H); $^{13}$C NMR (125 MHz, CDCl$_3$) δ 14.1, 14.2, 20.9, 21.1, 24.7, 27.9, 28.3, 28.5, 29.7, 34.6, 36.6, 42.6, 43.2, 48.7, 48.9, 49.1, 50.3, 50.8, 50.9, 55.0, 55.2, 55.4, 60.4, 68.1, 68.2, 68.4, 78.7, 79.2, 79.3, 79.4, 79.5, 82.9, 92.2, 92.4, 93.6, 93.8, 112.4, 112.5, 112.6, 112.7, 115.3, 115.5, 119.6, 119.7, 120.0, 121.1, 122.78, 122.81, 130.17, 130.24, 140.7, 140.8, 140.9, 141.0, 149.7, 151.45, 151.51, 151.8, 154.5, 154.8, 159.0, 159.06, 159.13, 161.8, 163.8; LC-TOF (M+H$^+$) calcd for C$_{36}$H$_{53}$F$_2$N$_4$O$_7$ 691.3882, found 691.3899.

Example 14

6-((3R,4R)-4-(2-((2,2-Difluoro-2-(3-fluorophenyl)ethyl) amino)ethoxy)pyrrolidin-3-yl)methyl)-4-methylpyridin-2-amine (23). To a solution of 22a (70 mg, 0.10 mmol) in MeOH (2 mL) was added 6 NHCl (4 mL) at room temperature. The mixture was stirred for 12 h and then concentrated. The crude product was purified by recrystallization (EtOH/H$_2$O) to give inhibitor 23 (38 mg, 97%): $^1$H NMR (500 MHz, D$_2$O) δ 2.29 (s, 3H), 2.78-2.81 (m, 2H), 2.95-3.05 (dd, J=8.0, 15.0 Hz, 1H), 3.15-3.20 (t, J=6.0, 1H), 3.31-3.35 (dd, J=3.0, 13.0 Hz, 1H), 3.40-3.55 (m, 3H), 3.63-3.66 (d, J=13.0 Hz, 1H), 3.71-3.79 (m, 1H), 3.87-3.95 (m, 3H), 4.24-4.26 (t, J=3.0 Hz, 1H), 6.55 (s, 1H), 6.64 (s, 1H), 7.25-7.29 (dt, J=2.5, 8.5 Hz, 1H), 7.34-7.36 (dd, J=2.5, 14.0 Hz, 1H), 7.38-7.40 (dd, J=2.5, 8.0 Hz, 1H), 7.49-7.52 (dd, J=6.0, 8.0 Hz, 1H); $^{13}$C NMR (125 MHz, D$_2$O) δ 21.0, 29.1, 41.3, 47.0, 47.5, 49.2, 51.5, 51.7, 51.9, 63.6, 78.0, 110.4, 112.3, 112.5, 114.0, 118.2, 118.4, 118.6, 121.0, 131.2, 131.3, 134.2, 145.5, 153.9, 158.1, 161.4, 163.3; LC-TOF (M+H$^+$) calcd for C$_{21}$H$_{28}$F$_3$N$_4$O 409.2215, found 409.2223.

Example 15

6-(((3R,4R)-4-(2-((2,2-Difluoro-2-(3-chlorophenyl) ethyl)amino)ethoxy)pyrrolidin-3-yl)methyl)-4-methylpyridin-2-amine (4). Inhibitor 4 was synthesized using a similar procedure to that of 23 (95%): $^1$H NMR (500 MHz, D$_2$O) δ 2.19 (s, 3H), 2.60-2.75 (m, 1H), 2.85-2.95 (m, 1H), 3.00-3.10 (t, J=11.0 Hz, 1H), 3.20-3.30 (m, 1H), 3.30-3.45 (m, 3H), 3.55-3.60 (d, J=13.0 Hz, 1H), 3.65-3.70 (m, 1H), 3.75-3.90 (m, 3H), 4.15 (d, J=3.0 Hz, 1H), 6.41 (s, 1H), 6.55 (s, 1H), 7.30-7.45 (m, 3H), 7.52 (s, 1H); $^{13}$C NMR (125 MHz, D$_2$O) δ 20.0, 29.2, 41.3, 41.4, 47.0, 47.4, 49.1, 51.7, 63.6, 78.3, 110.4, 114.0, 118.2, 123.39, 123.42, 123.47, 125.07, 125.12, 130.7, 131.5, 133.9, 134.4, 145.4, 153.9, 158.1; LC-TOF (M+H$^+$) calcd for C$_{21}$H$_{28}$ClF$_3$N$_4$O 425.1920, found 425.1919.

Example 16

6-(((3R,4R)-4-(2-((2,2-Difluoro-2-(2-chlorophenyl) ethyl)amino)ethoxy)pyrrolidin-3-yl)methyl)-4-methylpyridin-2-amine (24). Inhibitor 24 was synthesized using a similar procedure to that of 23 (95%): $^1$H NMR (500 MHz, D$_2$O) δ 2.19 (s, 3H), 2.60-2.75 (m, 1H), 2.85-2.95 (m, 1H), 3.03-3.08 (t, J=11.5 Hz, 1H), 3.19 (s, 1H), 3.21 3.25 (dd, J=3.0, 13.0 Hz, 1H), 3.35-3.42 (m, 3H), 3.52-3.58 (d, J=13.0 Hz, 1H), 3.63-3.66 (m, 1H), 3.82-3.88 (m, 1H), 3.90-4.00 (m, 2H), 4.14-4.16 (t, J=3.5 Hz, 1H), 4.15 (d, J=3.0 Hz, 1H), 6.42 (s, 1H), 6.54 (s, 1H), 7.30-7.35 (m, 1H), 7.40-7.45 (m, 2H), 7.55-7.60 (m, 1H); $^{13}$C NMR (125 MHz, D$_2$O) δ 21.0, 29.0, 41.2, 47.0, 47.4, 48.8, 49.2, 50.3, 50.5, 63.4, 78.2, 110.4, 113.9, 118.1, 127.57, 127.63, 127.70, 129.1, 130.8, 131.4, 131.5, 133.1, 145.5, 153.9, 158.1; LC-TOF (M+H$^+$) calcd for C$_{21}$H$_{28}$ClF$_3$N$_4$O 425.1920, found 425.1919.

Example 17

Compound 25. Inhibitor 25 was synthesized using a similar procedure to that of 23 (95%) as a mixture of two diastereomers: $^1$H NMR (500 MHz, D$_2$O) δ 2.19 (s, 3H), 2.65-2.75 (m, 2H), 2.85-2.95 (m, 1H), 3.03-3.11 (m, 1H), 3.20 (s, 1H), 3.21-3.25 (dd, J=3.0, 13.0 Hz, 1H), 3.30-3.45 (m, 4H), 3.50-3.58 (m, 2H), 3.60-3.66 (m, 1H), 3.80-3.85 (m, 1H), 4.14-4.16 (m, 1H), 5.80-6.00 (m, 1H), 6.46 (s, 1H), 6.50-6.55 (m, 1H), 7.00-7.15 (m, 3H), 7.30-7.41 (m, 1H); $^{13}$C NMR (125 MHz, D$_2$O) δ 21.0, 29.0, 29.1, 41.3, 41.4, 43.7, 43.9, 47.0, 47.1, 47.3, 48.7, 49.2, 49.3, 51.3, 51.5, 51.7, 51.8, 63.6, 63.9, 78.2, 88.4, 89.8, 110.4, 112.48, 112.54, 112.56, 112.61, 112.69, 112.72, 112.74, 114.0, 114.1, 116.3, 116.5, 116.6, 121.35, 121.40, 121.46, 121.49, 121.51, 130.85, 130.92, 131.0, 136.8, 136.99, 137.02, 145.60, 145.64, 153.85, 153.86, 158.11, 158.12, 161.6, 163.5; LC-TOF (M+H$^+$) calcd for C$_{21}$H$_{29}$F$_2$N$_4$O 391.2309, found 391.2288.

As demonstrated, the present invention provides a high-yield route for the synthesis of 1 and its derivative 10—the latter of which represents a compound otherwise inaccessible by the prior art—among other such selective nNOS inhibitors. For certain embodiments, 10 steps (e.g., three steps fewer than the prior art method) provides an overall yield of around 10% (~20-fold increase). Such a route provides, for instance, a practical method for a multi-gram scale synthesis of 1. It also enables a broader study of structure-activity relationships based on 1, which will be beneficial for further inhibitor development.

We claim:
1. A method of preparing a chiral pyrrolidine core compound, said method comprising;
providing an N-Boc-protected pyrrolidine-3,4-epoxide of a structure

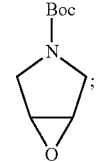

alkylating said eppxide with an N-Boc protected heterocyclic compound of the formula

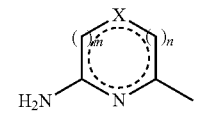

wherein X is selected from CH, C—CH$_3$, N, O, and S; and m and n are independently 0 or 1, provided at least one of m and n is 1, said alkylation providing a racemic alkyl-substituted trans-pyrrolidine alcohol;

protecting said amino grow on the heterocyclic compound with a Boc reagent;

resolving said racemic trans-alcohol by camphanic acid esterification, to provide separable cis-diastereomers; and hydrolysis of one said cis-enantiomer of said racemate, to provide a chiral 4-hydroxypyrrolidine compound.

2. The method of claim 1 wherein said alkylheterocyclic compound is an amino methylpyridine compound.

3. The method of claim 1 wherein said pyrrolidine alcohol is protected with a silyl chloride reagent before said amino group protection.

4. The method of claim 3 wherein said alcohol protection is removed before said camphanic acid esterification.

5. The method of claim 1 wherein said 4-hydroxypyrrolidine compound is allylated.

6. The method of claim 5 comprising oxidation of said allyl moiety of said chiral pyrrolidine compound to provide an aldehyde group, and reductive amination of said aldehyde group with an ethanamine.

7. The method of claim 6 comprising removal of three Boc-protecting groups.

\* \* \* \* \*